(12) United States Patent
Pipes et al.

(10) Patent No.: US 6,359,119 B1
(45) Date of Patent: Mar. 19, 2002

(54) FORMULATION OF TC AND RE CARBONYL COMPLEXES USING STANNOUS ION AS THE REDUCTANT FOR PERTECHNETATE AND PERRHENATE

(75) Inventors: David W. Pipes, Chesterfield; Mary E. Dyszlewski, Creve Coeur; Elizabeth G. Webb, St. Charles, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/576,960

(22) Filed: May 24, 2000

(51) Int. Cl.⁷ .................. C07F 13/00; A61K 51/00; G01N 33/534
(52) U.S. Cl. .................. 534/14; 424/1.57; 424/1.65; 424/1.69; 424/1.73; 435/7.24; 435/7.25; 435/372; 530/402; 530/811; 556/46
(58) Field of Search .................. 556/46; 534/14; 530/402, 811; 424/1.65, 1.57, 1.73, 1.69; 435/372, 7.24, 7.25

(56) References Cited

U.S. PATENT DOCUMENTS

| 4,232,000 A | 11/1980 | Fawzi |
|---|---|---|
| 4,233,284 A | 11/1980 | Fawzi |
| 4,427,647 A | * 1/1984 | Brockas et al. |

FOREIGN PATENT DOCUMENTS

| EP | 879606 | * 11/1998 |
|---|---|---|
| WO | 9630054 | 10/1996 |
| WO | 9848848 | 11/1998 |

OTHER PUBLICATIONS

Alberto R. et al. "Low–Pressure Synthesis of $[MX_3(CO)_3]^{2-}$ (M =Tc,Re; X =Cl⁻,Br) and Its Substitution Behaviour in Water and Organic Solvents", *The Journal of Nuclear Biology and Medicine*, Sep. 1994; 38:388–390.

* cited by examiner

*Primary Examiner*—Mary E. Ceperley
(74) *Attorney, Agent, or Firm*—Rothwell, Figg, Ernst & Manbeck

(57) ABSTRACT

The invention relates to novel aminocarboxylate ligands that are suitable for complexing with a radionuclide, and are useful as therapeutic agents and as imaging agents for diagnostic purposes. In accordance with the present invention, a method of preparing a compound of formula $$\text{fac-}[M(CO)_3(OH_2)_3]^+ \qquad (I)$$

wherein M is Mn, ⁹⁹ᵐTc, ¹⁸⁶Re or ¹⁸⁸Re,
involves reacting a metal in permetallate form with carbon monoxide and stannous ion. The compound of formula (I) can be reacted with a ligand $L_x$ to form a compound of the formula $$\text{fac-}[M(CO)_3 L_x]^n \qquad (II)$$

wherein M is as defined above, $L_x$ is a monodentate or multidentate ligand or a mixture of these ligands, and n is a charge of the ligand $L_x$ increased with one + charge. The invention also is directed to novel compounds, and kits for carrying out the disclosed methods.

17 Claims, No Drawings

FORMULATION OF TC AND RE CARBONYL COMPLEXES USING STANNOUS ION AS THE REDUCTANT FOR PERTECHNETATE AND PERRHENATE

FIELD OF THE INVENTION

The present invention relates to a novel method for preparing Mn, Tc and Re carbonyl complexes which are useful such as for imaging and therapeutic agents.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which, upon introduction to a biological subject, become localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

Technetium-99m ($^{99m}$Tc) is a radionuclide which is widely known for its uses in tissue imaging agents. Due to its safety and ideal imaging properties, this radionuclide is conveniently available commercially in the oxidized pertechnetate form ($^{99m}$TcO$_4^-$) hereinafter "pertechnetate-Tc99m". However, pertechnetate will not complex with the most commonly used biological carriers for radionuclide tissue imaging. Thus, technetium-labeled imaging agents are generally prepared by admixing a pertechnetate-Tc99m isotonic saline solution, a technetium reductant (reducing agent) such as stannous chloride or sodium dithionite, and a chelate conjugated to the desired peptide carrier agent for targeting the organ of interest. Alternatively, an intermediate transfer liquid-technetium 99m complex may be prepared prior to addition to the chelate-biological molecule to maintain the oxidation state within a desired level. Examples of such include $^{99m}$Tc-tartrate or $^{99m}$Tc-gluconate.

Another problem is that technetium-containing scintigraphic imaging agents are known to be unstable in the presence of oxygen, primarily since oxidation of the reductant and/or the technetium-99m destroys the reduced technetium-99m/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980, discloses the use of gentisic acid as a stabilizer.

In published PCT Application No. PCT/US98/07979 (International Publication No. WO 98/48848), which is incorporated herein in its entirety by reference, a method was disclosed for preparing a compound of the general formula (I): fac-[M(CO)$_3$(OH$_2$)$_3$]$^+$ wherein M is Mn, $^{99m}$Tc, $^{186}$Re or $^{188}$Re, by reacting a metal in the permetallate form with carbon monoxide and a reducing agent, characterized in that a mixture of a base, a reducing agent soluble in water but not substantially decomposed by water, and optionally a stabilizing agent is dissolved in a water containing solvent system containing a solution of the metal in the permanganate, pertechnetate or perrhenate form in the presence of carbon monoxide and optionally in the presence of a halide. The ligands disclosed for labeling biologically active molecules have a tendency to stabilize metals in their low oxidation states. These ligands have in common the presence of low-lying vacant orbitals of the correct symmetry to form pi-bonds by accepting electrons from filled metal d-orbitals, a phenomenon known as backbonding. The ligands indicated in the patent application include isonitriles, phosphines, thioethers, Schiff bases, and pyridine-, imidazole-, and pyrazole-type groups. In particular, the amino acid histidine is indicated as an ideal chelate. For some purposes a problem with using histidine and other unsaturated organic molecules as chelates is that the resulting labeled compound is highly lipophilic resulting in high liver and blood uptake. The predominant hepatobiliary uptake and clearance are for some purposes undesirable characteristics for the targeted imaging agents.

The publications and other materials used herein to illuminate the background of the invention or provide additional details respecting the practice, are incorporated by reference, and for convenience are respectively grouped in the appended List of References.

SUMMARY OF THE INVENTION

In accordance with the present invention, a method of preparing a compound of formula

$$\text{fac-[M(CO)}_3\text{(OH}_2\text{)}_3\text{]}^+ \quad \quad \quad (I)$$

wherein M is Mn, $^{99m}$Tc, $^{186}$Re or $^{188}$Re,
involves reacting a metal in permetallate form with carbon monoxide and a reducing agent, wherein the reducing agent comprises a stannous ion. The compound of formula (I) can be reacted with a ligand L$_x$ to form a compound of the formula

$$\text{fac-[M(CO)}_3\text{L}_x\text{]}^n \quad \quad \quad (II)$$

wherein M is as defined above, L$_x$ is a monodentate or multidentate ligand or a mixture of these ligands, and n is a charge of the ligand L$_x$ increased with one + charge. The invention also is directed to kits for performing the disclosed methods.

DETAILED DESCRIPTION OF THE INVENTION

The present invention relates to an improved method for synthesizing Tc(I) complexes using stannous ion as the reducing agent. For formulating Tc(I) complexes, e.g., [Tc(CO)$_3$(OH$_2$)$_3$]$^{30}$, the prior art methods have successfully used only the powerful reductants of borohydrides (BH$_3$ or BH$_4^-$). Attempts to use other reductants including stannous ion (Sn$^{2+}$) have resulted in labeling yields of approximately only 50%. The use of the more common Sn$^{2+}$ in radiopharmaceutical kits has certain advantages such as a wide pH range of use, known toxicity, familiarity with the FDA and perhaps better adaptability between Tc and Re formulations. In addition, stannous ion is less likely to interfere with the biological substrate or ligands which are ultimately labeled. The instant invention discloses a method of using Sn$^{2+}$ for the preparation of Tc-carbonyl complexes with yields of >80%, a clear improvement of the previous work.

It has normally been felt that to form Tc in oxidation state I as is the case of the Tc-carbonyl complexes formed according to this disclosure, a very strong reductant is needed, one with a negative value in the electrochemical series. The starting Tc compound is pertechnetate, $TcO_4^-$, which has Tc in oxidation state VII. To form the desired Tc-carbonyl complexes, it is necessary to reduce the Tc(VII) down to Tc(I).

Stannous ion is normally not thought of as a strong reductant because its electrochemical half equation is not very negative. In the presence of a 0.1 N acid, the electrochemical equation is:

$$Sn^{4+} + 2e^- \leftrightarrows Sn^{2+} \quad E° = +0.15 \text{ Volts}$$

The effect of pH upon this equation is usually forgotten. At a basic pH (>7) the reducing strength of stannous ion is changed as a result of a change in the reductant's mechanism. In a basic solution, a stannous hydroxide chemical species is present with a different mechanism and reductant strength which is capable of reducing the Tc(VII) down to Tc(I), especially with the aid of an appropriate transfer ligand such as pyrophosphate or another ligand such as tartrate, gluceptate, methylenediphosphonate or hydroxyethyldiphosphonate. In a basic solution (0.1 N NaOH, pH=13), the half equation is:

$$Sn(OH)_6^{2-} + 2e^- \leftrightarrows HSnO_2^- + 3OH^- + H_2O \quad E° = -0.96 \text{ Volt}$$

This shows that stannous ion is a strong reductant at a basic pH. This is comparable to the electrochemical half equation for borohydride which is the reductant used in the prior art to form the desired Tc carbonyl compounds. Borohydride has an E°=−1.2 Volts at pH 13.

Methods are disclosed for preparation of facial metal tricarbonyl compounds and further coordinated facial metal tricarbonyl compounds. The invention further relates to the use of said facial metal tricarbonyl compounds in the labeling of biologically active substrates and other ligands, and to a kit for preparing a facial metal tricarbonyl compound or further co-ordinated facial metal tricarbonyl compounds.

It is known in the art (Alberto et al., 1994a) that facial metal tricarbonyl complexes of radioactive metals of group 7B of the periodic table are very convenient starting materials for substitution reactions in organic solvents as well as in water, as these compounds are stable in water for weeks, even if exposed to air. Therefore said compounds will be very useful for the labeling of biologically active substrates, such as amino acids, peptides, proteins, sugars and any receptor binding molecules. A major drawback, however, of these compounds until now is that they have only been available from high temperature carbonylation reactions and with the aid of the pyrophoric and toxic and therefore dangerous reducing agent $BH_3$ (Alberto et al., 1994b).

It is the objective of the present invention to provide for a method of preparing facial metal tricarbonyl compounds of (radioactive) metals of group 7B with the aid of easily available and low-toxic starting materials at moderate temperature and at normal pressure of CO, in a reasonable time and with high yield.

Such a method will be a powerful tool that can be used for the synthesis of diagnostic and therapeutic agents, especially for the synthesis of said diagnostic and therapeutic agents derived from radioactive metals with a short lifetime, in order to have access to these labeled compounds in poorly equipped hospital laboratories. When the above mentioned diagnostic agent is labeled with a radionuclide it can be detected by the so-called single photon emission computerized tomography (SPECT), when it is labeled with a paramagnetic metal atom it can be detected by magnetic resonance imaging.

The above-defined objective can be achieved, according to the present invention, by a method of preparing a compound of the general formula $$\text{fac-}[M(CO)_3(OH_2)_3]^+ \tag{I}$$

wherein M is Mn, $^{99m}$Tc, $^{186}$Re or $^{188}$Re,
by reacting a metal in the permetallate form ($MO_4^-$ form) with carbon monoxide and a reducing agent comprising $Sn^{2+}$.

The metal M is preferably $^{99m}$Tc, $^{186}$Re or $^{188}$Re, as these radionuclides, when used in diagnostic or therapeutic agents, have the advantage that they can be applied in very low concentrations, which minimizes the risk of toxicity.

It is very surprising that a quantitative reduction of permetallates in water containing solvent systems can be achieved at moderate temperature and in reasonable times with reducing agents that are nucleophilic and that are generally considered as less reactive than the electrophilic reducing agent $BH_3$ known in the art.

The method of the invention can be easily performed just by mixing the permetallate solution with the other reagents in the presence of carbon monoxide. The permetallate solution may optionally contain halide ions needed for the elution of the permetallate from a generator. The carbon monoxide may be supplied by using a closed system with an atmosphere containing a sufficient amount of carbon monoxide, or by flushing the carbon monoxide gas through the solution. Preferably the gas is substantially pure carbon monoxide. For the reduction the reducing agent is one comprising stannous ions. In preferred embodiments, the mixture includes lactose which is present as a bulking agent.

The reducing agent is reacted with the permetallate in a molar ratio higher than 3, preferably higher than 10 and most preferably higher than 100. The reduction reaction can be performed at a temperature between 20° C. and 150° C. The preferred reaction temperature is approximately 100° C. The heating of the reaction mixture can be performed in the normal way but also by microwave heating. The reaction can also be performed by the application of ultrasound, e.g., by carrying out the reactions in an ultrasonic bath at room temperature, normally leading to the same reaction rate at lower reaction temperature.

The compound of the general formula (I) obtained is very suitable for the labeling of biologically active substrates, such as amino acids, peptides, proteins, sugars, small receptor binding molecules or cells.

Examples of peptides that may be labeled are growth factors, somatostatin, bombesin, insulin, LHRH, gastrin, gastrin releasing peptide, thyrotropin releasing hormone, thyroid stimulating hormone, prolactin, vasoactive intestinal peptide (VIP), pituitary adenylate cyclase-activating polypeptide (PACAP), angiotensin, neurotensin, interferons, IL-1, IL-4 and IL-6, monoclonal antibodies and their analogues and derivatives. After labeling with a suitable labeling substance these peptides can, e.g., be used in the detection and localization of treatment of malignant human tumors.

Examples of sugars that may be labeled are glucose and deoxyglucose and derivatives of said compounds.

Small receptor binding molecules are defined as non-peptide molecules which are binding to a receptor and normally have a molecular mass below approximately 500 Daltons.

Examples of small receptor binding molecules that may be labeled are substances for the serotonergic system as described in WO 96/30054, or substances for the dopaminergic system (e.g., raclopride, β-CIT, lisuride), for the cholinergic system (e.g., epibatidine), for the glutaminergic system (e.g., mematine) or for the benzodiazepine system (e.g., flumazenil, iomazenil). Examples of metabolic active molecules that may be labeled are DOPA, Tyrosine, mIBG, MAO-I and analogues thereof.

Examples of cells that may be labeled are red and white blood cells.

As a result of the labeling of (biologically active) substrates with a compound of the general formula I, a further coordinated compound of the general formula

  (II),

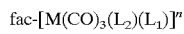  (III), or

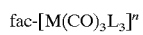  (IV), is obtained wherein:

M is Mn, $^{99m}$Tc, $^{186}$Re or $^{188}$Re;
$L_1$ is a monodentate ligand;
$L_2$ is a bidentate ligand;
$L_3$ is a tridentate ligand; and
n is the sum of the charge of the ligands $L_1$, $L_2$ and $L_3$ increased with one + charge.

When the ligand $L_1$, $L_2$ or $L_3$ before and/or after labeling with the facial metal tricarbonyl compound is the biologically active molecule, the present invention gives easy access to compounds that directly can be used as a diagnostic and therapeutic agent.

Examples of monodentate ligands within the definition of $L_1$, $L_2$ and $L_3$ are (biologically active) substrates bearing groups such as phosphines, isonitriles, nitriles, imidazoles, thioethers and pyridine-like aromatic amines.

Examples of bidentate ligands within the definition of $L_2$ and $L_3$ are (biologically active) substrates bearing pyridine, imidazole or pyrazole groups, such as histidine, histamine, functionalized imidazole systems, bidentate thioethers, bidentate isocyanides, Schiff-base type ligands and picolinic acid.

Examples of tridentate ligands within the definition of $L_3$ are tris-pyrazolyl borate, tris-pyrazolylmethane, tris-imidazolyl borate, tris-pyrazolylmethane, 1,4,7-trithiacyclononane (9-aneS$_3$) and triazacyclononane (9-aneN$_3$), histidine, methionine, cysteine derivatized at the thiol group to give a thioether and cyclopentadienyl derivatives.

In some cases it may be advantageous to prepare the radiolabelled bioactive compound in one step. This objective can be achieved according to the present invention, with a method of preparing a compound of the general formula

  (II),

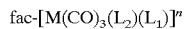  (III), or

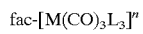  (IV), wherein:

fac-[M(CO)$_3$(L$_1$)$_3$]$^n$ (II),
fac-[M(CO)$_3$(L$_2$)(L$_1$)]$^n$ (III), or
fac-[M(CO)$_3$(L$_3$)]$^n$ (IV),
wherein:
M is Mn, $^{99m}$Tc, $^{186}$Re or $^{188}$Re;
$L_1$ is a monodentate ligand;
$L_2$ is a bidentate ligand;
$L_3$ is a tridentate ligand; and
n is the sum of the charge of the ligands $L_1$, $L_2$ and $L_3$ increased with one + charge;

characterized in that a mixture of a base, ligands $L_1$ or $L_2$ or $L_3$, a stannous ion, and optionally a stabilizing agent is dissolved in a water containing solvent system containing a solution of the metal in the permanganate, pertechnetate or perrhenate form in the presence of carbon monoxide and optionally in the presence of halide.

Especially in the case of radiolabelled compounds it is frequently impossible to put the ready-for-use composition at the disposal of the user, in connection with the often poor shelf life of the radiolabelled compound and/or the short half-life of the radionuclide used. In such cases the user will carry out the labeling reaction with the metal in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive labeled composition by using the facilities that are at his disposal. Therefore the invention also relates to a kit for preparing a labeling composition, which labeling composition contains a compound of formula I as the labeling agent.

Such a kit for the labeling of a biologically active substrate, according to the present invention, comprises (i) a reducing agent comprising stannous ion, (ii) if desired, a stabilizing agent and/or a chelator, e.g., pyrophosphate or glucoheptonate, and (iii) if desired one or more inert pharmaceutically acceptable carriers and/or formulating agents and/or adjuvants, e.g., lactose or inositol, at least one of said ingredients (i) to (iii) being stored in a container having an atmosphere containing a sufficient amount of carbon monoxide, or said ingredients (i) to (iii) being independently combined, and (iv) instructions for use with a prescription for reacting the ingredients of the kit with a metal selected from the group consisting of Mn, $^{99m}$Tc, $^{186}$Re or $^{188}$Re in the form of permetallate solution. Preferably, the kit comprises a lyophilized formulation including pyrophosphate or gluceptate, SnCl$_2$, and lactose, the mixture being sealed in a container having a headspace comprising carbon monoxide, most preferably substantially pure carbon monoxide. In other embodiments, the kit can include a metal (M) as defined above. In still further embodiments, the kit can include a ligand (L$_x$), which preferably is a multidentate aminopolycarboxylate ligand.

It is the merit of the present invention, disclosing an easy way of preparing facial tricarbonyl metal compounds within a time-frame that is reasonable compared with the half-life time of the radioactive isotopes involved, and with high yields, that a kit can be prepared for the labeling of biologically active substrates with said facial tricarbonyl metal compounds.

In some cases it may be advantageous to enclose a bioactive substrate in the kit so that a kit is obtained for the preparation of a radiopharmaceutical composition.

Alternatively the biologically active compound is formed upon the reaction of the ligand with the facial metal tricarbonyl compound.

Such a kit for the preparation of a diagnostic and therapeutic pharmaceutical composition, according to a different embodiment of the present invention, comprises (i) a suitable substrate to be labeled with a metal selected from the group consisting of Mn, $^{99m}$Tc, $^{186}$Re or $^{188}$Re, (ii) a reducing agent comprising stannous ion, (iii) if desired, a stabilizing agent and/or a chelator, (iv) if desired one or more inert pharmaceutically acceptable carriers and/or formulating agents and/or adjuvants, at least one of said ingredients (i) to (iv) being stored in a container having an atmosphere containing a sufficient amount of carbon monoxide, or said ingredients (i) to (iv) independently being combined, and (v) instructions for use with a prescription for reacting the ingredients of the kit with said metal in the form of a permetallate solution.

The preparation of the diagnostic and therapeutic pharmaceutical composition with the aid of the above mentioned kit enclosing a (biologically active) substrate can take place in two alternative embodiments. In the first embodiment the facial tricarbonyl metal compound is prepared first and then reacted with the substrate to be labeled. In the second embodiment the reduction step is carried out in the presence of the substrate to be labeled, directly leading to the labeled compound.

The invention will now be described in greater detail with reference to the following specific Examples, which are offered by way of illustration and are not intended to limit the invention in any manner. Standard techniques well known in the art or the techniques specifically described below are utilized.

EXAMPLE 1

Synthesis of [Tc(CO)$_3$(OH$_2$)$_3$]$^+$ Using SnCl$_2$ and Pyrophosphate or Gluceptate Kits were prepared for performing the synthetic reactions. The first kits and results are shown in Table 1.

TABLE 1

| Reagent/formulation | Kit A | Kit B | Kit C |
|---|---|---|---|
| Stannous chloride dihydrate (SnCl$_2$.H$_2$O) | 0.7 mg | 3.2 mg | 1.6 mg |
| Gluceptate, sodium salt | 50 mg | — | — |
| Pyrophosphate, sodium salt | — | 11.9 mg | 6 mg |
| pH (adjusted with 1 N NaOH) | 10.5 | 7.3 | 7 |
| Volume (0.9% saline) | 1.3 mL | 1.3 mL | 1.1 mL |
| Headspace purged with CO gas | (10 cc vial) | (10 cc vial) | (10 cc vial) |
| Heat | 100° C./30 minutes | 75° C./30 minutes | 75° C./30 minutes |
| Analysis (HPLC) | approx. 42% $^{99m}$Tc(CO)$_3$(aquo)$_3$$^+$ | approx. 80% $^{99m}$Tc(CO)$_3$(aquo)$_3$$^+$ | approx. 84% $^{99m}$Tc(CO)$_3$(aquo)$_3$$^+$ |

Further work was performed using the following formulations. Five kits were formulated with different amounts of stannous ion and pyrophosphate ligand (potential transfer ligand for chelate attached to bioactive compounds). The five kits contained the following:

TABLE 2

| Ingredients | Kit 1 | Kit 2 | Kit 3 | Kit 4 | Kit 5 |
|---|---|---|---|---|---|
| Sodium pyrophosphate | 5.0 mg | 5.0 mg | 10.1 mg | 10.1 mg | 10.3 mg |
| Lactose H$_2$O | 20.1 mg | 20.1 mg | 20.2 mg | 20.1 mg | 20.2 mg |
| SnCl$_2$ | 0.51 mg | 1.13 mg | 0.50 mg | 1.10 mg | 3.03 mg |
| pH | 6.1 | 5.0 | 6.5 | 6.0 | 3.4 |

To each lyophilized kit, 1 mL $^{99m}$TcO$_4$$^-$ in 0.9% NaCl was added and the vial (solution) was heated at 100° C. for 15 minutes. Labeling was very high (>99% of the $^{99m}$TcO$_4$$^-$ was reacted with less than 1% TcO$_4$$^-$ remaining, with approximately 80% of the label appearing in the desired product, the rest appearing in undesired products). The reaction products were assayed by HPLC as follows: Column: Vydac-218 TP54 C-18, 250×4.6 mm; Flow rate: 1 mL/minute; Mobile Phase A: 0.05 M triethylamine phosphate (TEAP), pH 2.25; Mobile Phase B: methanol; Detector: Beckman Model 170 Radiometric Detector. A gradient with linear mixing was used as shown in Table 3.

TABLE 3

| Time Interval | Percent Mobile Phases |
|---|---|
| 0–3 minutes | 100% A |
| 3–6 minutes | 100% A to 75% A/25% B |
| 6–9 minutes | 75% A/25% B to 66% A/34% B |
| 9–20 minutes | 66% A/34% B to 100% B |

Results are shown in Tables 4 and 5. The 3' peak is an impurity that elutes prior to the $^{99m}$Tc-carbonyl. The values in Tables 4 and 5 do not add to 100% because other products, including some $^{99m}$TcO$_2$, were also present.

TABLE 4

| | | | Initial % Radiochemical Purity | | |
|---|---|---|---|---|---|
| Kit # | $^{99m}$TcO$_4$$^-$ volume | Amount of activity | 3' peak | $^{99m}$Tc-carbonyl | $^{99m}$TcO$_4$$^-$ |
| 1 | 1 mL | 54.5 mCi | 1.9 | 80.5 | 10.6 |
| 2 | 1 mL | 56.7 mCi | 8.5 | 77.9 | 4.1 |
| 3 | 1 mL | 48.0 mCi | 1.7 | 79.3 | 10.9 |
| 4 | 1 mL | 45.5 mCi | 2.7 | 78.1 | 9.6 |
| 5 | 1 mL | 40.0 mCi | 10.3 | 76.7 | 0 |

TABLE 5

| | | | 6 Hour % Radiochemical Purity | | |
|---|---|---|---|---|---|
| | pH at 6 Hours | mg tin detected* | 3' peak | $^{99m}$Tc-carbonyl | $^{99m}$TcO$_4$$^-$ |
| 1 | 5.67 | 0.282 | 0 | 84.3 | 8.3 |
| 2 | 4.58 | 0.902 | 7.0 | 72.8 | 1.6 |
| 3 | 6.22 | 0.395 | 3.2 | 79.2 | 9.8 |
| 4 | 5.63 | 0.902 | 3.4 | 80.2 | 10.4 |
| 5 | 3.77 | 2.707 | 8.6 | 74.4 | 0 |

*The amount of tin detected after lyophilization by a method that has not been validated.

After initial labeling (reduction of $^{99m}$TcO$_4$$^-$ and formation of Tc(CO)$_3$(OH$_2$)$_3$$^+$ complex), this compound was then reacted with an amino acid (histidine) to simulate the labeling of a chelate that may be used to attach the Tc-99m to an imaging compound such as a peptide or antibody or other bioactive molecule. For this reaction, each kit was reconstituted with 1.0 mL $^{99m}TcO_4^-$ in saline and reacted as described, then 0.2 mL of the kit was incubated with 1 mg of histidine at 75° C. for one hour. Quality control was performed on the whole preparation and histidine reaction, and the pH of each reaction was measured the following morning. Results are shown in Tables 6 and 7.

TABLE 6

Whole Kit without Histidine

| Kit # | Amount of Activity | 3' peak | $^{99m}Tc$-carbonyl | $^{99m}TcO_4^-$ | $^{99m}Tc$-$(CO)_3His$ | pH |
|---|---|---|---|---|---|---|
| 1 | 73.9 mCi | 6.6 | 84.7 | 5.7 | — | 5.60 |
| 2 | 72.6 mCi | 14.2 | 61.1 | 0 | — | 4.23 |
| 3 | 73.0 mCi | 3.1 | 80.7 | 9.7 | — | 6.17 |
| 4 | 67.0 mCi | 18.3 | 79.3 | 1.6 | — | 5.50 |
| 5 | 65.5 mCi | 22.9 | 66.5 | 0 | — | 3.65 |

TABLE 7

Histidine reaction

| Kit # | Amount of Activity | 3' peak | $^{99m}Tc$-carbonyl | $^{99m}TcO_4^-$ | $^{99m}Tc$-$(CO)_3His$ | pH |
|---|---|---|---|---|---|---|
| 1 | 13.6 mCi | 7.0 | 13.0 | 22.4 | 51.6 | 6.74 |
| 2 | 13.4 mCi | 67.2 | 0 | 10.0 | 11.6 | 6.44 |
| 3 | 13.0 mCi | 8.2 | 0 | 19.0 | 67.9 | 6.82 |
| 4 | 11.3 mCi | 33.5 | 0 | 6.1 | 53.8 | 6.50 |
| 5 | 10.8 mCi | 86.1 | 0 | 0.1 | 4.3 | 5.94 |

However a mixture of what is believed to be Tc-carbonyl-ligand products was seen, where ligand was the pyrophosphate (or gluceptate if that were used instead of pyrophosphate) molecule. In the case of the Tc-CO-pyrophosphate complex mixture, addition of an excess amount histidine (3 mg) and heating for 30 minutes produced greater than 80% [Tc(CO)$_3$(histidine)] complex as shown by HPLC analysis. In the case where gluceptate was used in place of pyrophosphate to yield a Tc-CO-gluceptate complex, purging the solution with CO and reheating for 15 minutes increased the amount of [Tc(CO)$_3$(OH$_2$)$_3$]$^+$. Formulation studies with the pyrophosphate kits without the addition of CO produced no such complexes.

These studies indicate that the [Tc(CO)$_3$(OH$_2$)$_3$]$^+$ complexes can be prepared in high yields using stannous ion as the reductant. Additional transfer ligands besides pyrophosphate include phosphonates such as MDP, HEDP, HDP, etc., and ligands such as tartrate, gluceptate, etc. and carboxylic acids such as gentisic acid, ascorbic acid or oxalic acid, etc. or simple amino acids or mixed acid-amino compounds such as glycine or nicotinic acid or even histidine.

LIST OF REFERENCES

Alberto R, et al. (1994a). *J. Nucl. Biol. Med.* 38:388–90.
Alberto R, et al. (1994b). "Low CO pressure synthesis of (NEt)$_2$[MX$_3$(CO)$_3$] (M=Tc, Re) and its Substitution Behaviour in Water and Organic Solvents." *Technetium in Chemistry and Nuclear Medicine*, No 4, Cortina International, Milano.
U.S. Pat. No. 4,232,000, Fawzi, issued Nov. 4, 1980.
U.S. Pat. No. 4,233,284, Fawzi, issued Nov. 11, 1980.
WO 98/48848
WO 96/30054

What is claimed is:

1. A method of preparing a compound of formula $$\text{fac-}[M(CO)_3(OH_2)_3]^+ \quad (I)$$

wherein M is Mn, $^{99m}$Tc, $^{186}$Re or $^{188}$Re, comprising reacting a metal in permetallate form in a mixture with carbon monoxide and a reducing agent, wherein said reducing agent comprises stannous ion.

2. The method of claim 1 wherein said mixture further includes a stabilizing agent.

3. The method of claim 1 wherein said reducing agent forms a stannous ion.

4. The method of claim 1 wherein said reducing agent is a stannous salt.

5. The method of claim 1 wherein said reducing agent is selected from the group consisting of SnCl$_2$, SnCl$_2$ H$_2$O, SnF$_2$, SnBr$_2$, SnCl$_2$ 2H$_2$O, SnI$_2$, and SnSO$_4$.

6. The method of claim 1 wherein said mixture further includes lactose.

7. The method of claim 1 wherein said mixture further includes pyrophosphate or gluceptate.

8. A method of preparing a compound of formula $$\text{fac-}[M(CO)_3L_x]^n \quad (II)$$

wherein:

| M | is Mn, $^{99m}$Tc, $^{186}$Re or $^{188}$Re; |
|---|---|
| L$_x$ | is i) three monodentate ligands ii) one monodentate ligand and one bidentate ligand, or iii) one tridentate ligand; and |
| n | is a charge of the ligand L$_x$ increased with one + charge; comprising reacting a compound of formula (I) prepared according to claim 1 with ligand L$_x$. |

9. The method of claim 8, wherein the reaction with ligand L$_x$ takes place in the presence of a halide or a halide-like salt.

10. The method of claim 9 wherein said halide-like salt is selected from the group consisting of acetates, phosphates and sulfates.

11. The method of claim 8 wherein L$_x$ comprises an aminopolycarboxylate.

12. The method of claim 8 wherein L$_x$ comprises a biologically active substrate selected from the group consisting of amino acids, peptides, proteins, sugars, small receptor binding molecules and body cells.

13. The method of claim 8 wherein said method is performed between about 20° C. and 150° C.

14. The method of claim 8 wherein said method is performed at about 100° C.

15. The method of claim 11 wherein said aminopolycarboxylate ligand is selected from the group consisting of diethylenetriamine-pentaacetic acid (DTPA), ethylenediaminetetraacetic acid (EDTA), 1,4,7,10-tetraazacyclododecane-1,4,7,10-tetraacetic acid (DOTA), iminodiacetic acid (IDA), nitrilotriacetic acid (NTA), and triazacyclononanetriacetate.

16. The method of claim 11 wherein said ligand is not bidentate.

17. The method of claim 11 wherein said ligand is tridentate.

* * * * *